(12) United States Patent
Nagai et al.

(10) Patent No.: US 9,243,993 B2
(45) Date of Patent: Jan. 26, 2016

(54) SAMPLE ANALYZER AND SAMPLE ANALYZING METHOD

(75) Inventors: Takaaki Nagai, Kobe (JP); Masaharu Shibata, Kobe (JP); Noriyoshi Yoshida, Kobe (JP); Shoichiro Asada, Akashi (JP)

(73) Assignee: SYSMEX CORPORATION, Hyogo (JP)

( * ) Notice: Subject to any disclaimer, the term of this patent is extended or adjusted under 35 U.S.C. 154(b) by 817 days.

(21) Appl. No.: 11/374,109

(22) Filed: Mar. 14, 2006

(65) Prior Publication Data

US 2006/0210438 A1    Sep. 21, 2006

(30) Foreign Application Priority Data

Mar. 17, 2005    (JP) .................................. 2005-077723
Mar. 17, 2005    (JP) .................................. 2005-078117

(51) Int. Cl.
*G01N 33/00*    (2006.01)
*G01N 15/14*    (2006.01)
(Continued)

(52) U.S. Cl.
CPC .............. *G01N 15/14* (2013.01); *G01N 15/147* (2013.01); *G01N 2015/008* (2013.01);
(Continued)

(58) Field of Classification Search
CPC ................ G01N 15/14; G01N 15/147; G01N 2015/0069; G01N 2015/0073; G01N 2035/1032; G01N 2015/0084; G01N 2015/1486; G01N 2035/0094
USPC .............................................. 422/73; 436/43
See application file for complete search history.

(56) References Cited

U.S. PATENT DOCUMENTS 5,656,499 A    8/1997    Chupp et al.
5,675,760 A    10/1997    Asano et al.
(Continued)

FOREIGN PATENT DOCUMENTS

EP    0645631 A2    3/1995
EP    0 867 724 A2    9/1998
(Continued)

OTHER PUBLICATIONS

XE-2100 Operator'S Manual, Chapter 7.
(Continued)

*Primary Examiner* — Rebecca M Fritchman
(74) *Attorney, Agent, or Firm* — Sughrue Mion, PLLC

(57) ABSTRACT

A sample analyzer capable of operating in a first measuring mode for measuring a sample and a second measuring mode for measuring a sample, comprising: a sample provider for providing a sample; a common reagent provider for providing a common reagent used in the first measuring mode and the second measuring mode; a special reagent provider for providing a special reagent used in the second measuring mode; a mode selector for selecting one of the first measuring mode and the second measuring mode; a measuring section for measuring the sample; and wherein in the first measuring mode, the sample provider and the common reagent provider operate so as to make a first mode sample comprising the sample and the common reagent, and the measuring section operates so as to measure the first mode sample, and in the second measuring mode, the sample provider, the common reagent provider and the special reagent provider operate so as to make a second mode sample comprising the sample, the common reagent and the special reagent, and the measuring section operates so as to measure the second mode sample, is disclosed. A sample analyzing method is also disclosed.

20 Claims, 16 Drawing Sheets

(51) Int. Cl.
G01N 33/50 (2006.01)
G01N 15/00 (2006.01)
G01N 35/00 (2006.01)
G01N 35/10 (2006.01)

(52) U.S. Cl.
CPC ............... G01N 2015/0069 (2013.01); G01N 2015/0073 (2013.01); G01N 2015/0084 (2013.01); G01N 2015/1486 (2013.01); G01N 2035/0094 (2013.01); G01N 2035/1032 (2013.01)

(56) References Cited

U.S. PATENT DOCUMENTS

| | | |
|---|---|---|
| 5,812,419 A | 9/1998 | Chupp et al. |
| 6,333,197 B1 | 12/2001 | Le Comte et al. |
| 2001/0027269 A1 | 10/2001 | Tanaka |
| 2003/0032193 A1 | 2/2003 | Narisada |

FOREIGN PATENT DOCUMENTS

| | | |
|---|---|---|
| EP | 1 378 750 A1 | 1/2004 |
| JP | 5-40085 A | 2/1993 |
| JP | 7-085168 A | 3/1995 |
| JP | 2001-83165 A | 3/2001 |
| JP | 2001-281260 A | 10/2001 |
| JP | 2002-040035 A | 2/2002 |
| JP | 2003-106984 A | 4/2003 |
| WO | WO 2004/057308 | 7/2004 |

OTHER PUBLICATIONS

XE-3000 Operator'S Manual, Chapter 10.
Chinese Patent Office, "Office Action," issued in connection with Chinese Patent Application No. 200610071737.8, dated Dec. 23, 2011.

SAMPLE ANALYZER AND SAMPLE ANALYZING METHOD

FIELD OF THE INVENTION

The present invention relates to a sample analyzer and sample analyzing method.

BACKGROUND

Red blood cells, platelets, and white blood cells are suspended in the plasma of peripheral blood. Specimens are frequently examined since a great deal of clinical information can be obtained by blood analyses that examine these cells.

Basic items in blood examinations include measurement of the number of red blood cells, number of platelets, number of white blood cells, and hemoglobin concentration in the blood, and a hematocrit value is determined from these measurement results. The measurement of these values is generally referred to as CBC (complete blood count), and hemocytometers are widely used to determine CBC.

Hemocytometers allocate a blood sample into a plurality of aliquots. For example, a first aliquot may be diluted with a dilution liquid and used to measure the red blood cell count and platelet count. A second aliquot may be added with a hemolytic agent to hemolyze the red blood cells and used to measure white blood cells. A third aliquot may be used to measure hemoglobin concentration by adding a hemolytic agent to release the hemoglobin in the red blood cells. A hemocytometer performs these measurements and determines the hematocrit value.

The measurement of a white blood cell count is added to a white blood cell classification examination in order to provide clinical information more sophisticated than CBC, and the white blood cell classification examinations are widely performed to classify white blood cells as lymphocytes, monocytes, neutrophils, eosinophils, and basophils.

White blood cell classification methods classify white blood cells based on optical signals or electrical signals of scattered light, fluorescent light and so on, or combinations thereof, using stains to stain particles and hemolytic agents capable of preserving the cellular morphology of the white blood cell.

An example of a hemocytometer capable of white blood cell classification is the model XE-2100 manufactured by Sysmex Corporation.

The XE-2100 allocates a blood sample into a blood for measurement of a red blood cell count and platelet count, blood for measurement of hemoglobin concentration, and blood for measurement of white blood cell. The XE-2100 further allocates the blood for measurement of white blood cell into two aliquots; a WBC count reagent is added to one aliquot and the number of white blood cells and number of basophils are counted, and a WBC classifying reagent is added to the other aliquot and the white blood cells are classified into four classification types, and both of these measurement results are used as the basis for the white blood cell count and the white blood cell classifications.

The XE-2100 is configured so as to be capable of operating in a first mode that measures the white blood cell count, but does not classify the white blood cells, and a second mode that measure the white blood cell count and classifies the white blood cells. The XE-2100 requires two aliquots to measure the white blood cell count and perform the white blood cell classification in the second mode. Furthermore, since white blood cell classification is generally performed less frequently than measurement of the white blood cell count, the special reagent required for white blood cell classification in conventional hemocytometers is wasted when the white blood cell classification reagent use period expires.

U.S. Pat. No. 5,656,499 also discloses another hemocytometer. This hemocytometer has a plurality of mixing chambers for preparing mixed preparations corresponding to a plurality of aliquots. A first aliquot is subjected to hemolytic processing and thereafter scattered light from the cells is detected at multiple angles using an optical flow cell/transducer to measure the number of white blood cells and perform white blood cell classification. A second aliquot is subjected to dilution processing and thereafter the change in impedance when the cells pass through an orifice is detected by an impedance transducer to measure the red blood cell count and platelet count. A third aliquot is subjected to hemolytic processing and thereafter the light optical density of the hemolytic sample is detected by an HGB (hemoglobin) transducer to measure the HGB concentration.

SUMMARY

The scope of the present invention is defined solely by the appended claims, and is not affected to any degree by the statements within this summary.

A first aspect of the present invention is a sample analyzer capable of operating in a first measuring mode for measuring a sample and a second measuring mode for measuring a sample, comprising:

a sample provider for providing a sample;

a common reagent provider for providing a common reagent used in the first measuring mode and the second measuring mode;

a special reagent provider for providing a special reagent used in the second measuring mode;

a mode selector for selecting one of the first measuring mode and the second measuring mode;

a measuring section for measuring the sample; and wherein in the first measuring mode, the sample provider and the common reagent provider operate so as to make a first mode sample comprising the sample and the common reagent, and the measuring section operates so as to measure the first mode sample, and in the second measuring mode, the sample provider, the common reagent provider and the special reagent provider operate so as to make a second mode sample comprising the sample, the common reagent and the special reagent, and the measuring section operates so as to measure the second mode sample.

A second aspect of the present invention is a sample analyzer capable of operating in a first measuring mode for measuring a sample and a second measuring mode for measuring a sample, comprising:

a container used to make a first mixture used in the first measuring mode and a second mixture used in the second measuring mode;

a common reagent provider for providing a common reagent, used to make the first mixture and the second mixture, in the container;

a special reagent provider for providing a special reagent, used to make the second mixture, in the container; and a controller for controlling an operation of the common reagent provider, and the special reagent provider;

wherein in the second measuring mode, the controller makes the common reagent provider and the special reagent provider operate sequentially so as to (a) provide the special reagent in the container, and then (b) provide the common reagent in the container.

A third aspect of the present invention is a sample analyzing method for analyzing a sample with a sample analyzer capable of operating in a first measuring mode and a second measuring mode, comprising steps of:

(a) selecting one of the first measuring mode and the second measuring mode;

(b) making a first mode sample comprising a sample and a common reagent, and measuring the first mode sample; and (c) making a second mode sample comprising a sample, the common reagent, and a special reagent, and measuring the second mode sample;

wherein the step (b) is implemented in the first measuring mode and the step (c) is implemented in the second measuring mode.

A fourth aspect of the present invention is a sample analyzer for analyzing a sample, comprising:

a container;

a sample provider for providing the sample to the container;

a first reagent provider for providing a first reagent to the container to make a first mixed sample, which comprises the sample and the first reagent, in the container;

a second reagent provider for providing a second reagent to the container to make a second mixed sample, which comprises the sample, the first reagent, and the second reagent, in the container;

a first measuring section for measuring the first mixed sample;

a first mixed sample provider for providing the first mixed sample from the container to the first measuring section;

a second measuring section for measuring the second mixed sample; and a second mixed sample provider for providing the second mixed sample from the container to the second measuring section;

wherein the first mixed sample provider operates so as to provide a part of the first mixed sample from the container to the first measuring section; and wherein the second reagent provider provides the second reagent to the container which contains another part of the first mixed sample.

A fifth aspect of the present invention is a sample analyzing method for analyzing a sample, comprising steps of:

mixing the sample and a first reagent to make a first mixed sample which comprises the sample and the first reagent;

providing a part of the first mixed sample to a first measuring section;

mixing another part of the first mixed sample and a second reagent to make a second mixed sample which comprises the sample, the first reagent, and the second reagent;

providing the second mixed sample to the second measuring section;

measuring the first mixed sample by the first measuring section; and measuring the second mixed sample by the second measuring section.

A sixth aspect of the present invention is a blood analyzer for analyzing a blood sample, comprising:

a blood sample provider for providing a first blood sample and a second blood sample, the first and second blood samples being split from a blood sample;

a first sample preparation section for preparing a first measurement sample for measurement of red blood cells and/or platelets and a second measurement sample for measurement of hemoglobin, from the first blood sample provided by the blood sample provider;

a second sample preparation section for preparing a third measurement sample for measurement of white blood cells, from the second blood sample provided by the blood sample provider;

a first measuring section for measuring the first measurement sample;

a second measuring section for measuring the second measurement sample; and a third measuring section for measuring the third measurement sample.

A seventh aspect of the present invention is a blood analyzer for analyzing a blood sample, comprising:

a blood sample splitter for splitting a blood sample into two aliquots;

a sample preparation section for preparing a first measurement sample for measurement of red blood cells and/or platelets, a second measurement sample for measurement of hemoglobin, and a third measurement sample for classification and counting of white blood cells, from the two aliquots split by the blood sample splitter;

a first measuring section for measuring the first measurement sample;

a second measuring section for measuring the second measurement sample; and a third measuring section for measuring the third measurement sample.

A eighth aspect of the present invention is a blood analyzer capable of operating in a first measuring mode for measuring a blood sample and a second measuring mode for measuring a blood sample, comprising:

a sample splitter for splitting a blood sample;

a first reagent provider for providing a red blood cell reagent;

a second reagent provider for providing a first white blood cell reagent;

a third reagent provider for providing a second white blood cell reagent;

a fourth reagent provider for providing a hemoglobin reagent;

a first measuring section for measuring a red blood cell sample which comprises a first blood sample split by the sample splitter from the blood sample and the red blood cell reagent provided by the first reagent provider, for measurement of red blood cells;

a second measuring section for measuring one of a first white blood cell sample which comprises a second blood sample split by the sample splitter from the blood sample and the first white blood cell reagent provided by the second reagent provider, for counting of white blood cells, and a second white blood cell sample which comprises the second blood sample split by the sample splitter from the blood sample and the second white blood cell reagent provided by the third reagent provider, for classification and counting of the white blood cells;

a third measuring section for measuring a hemoglobin sample which comprises a third blood sample split by the sample splitter from the blood sample and the hemoglobin reagent provided by the fourth reagent provider for measurement of hemoglobin; and a mode selector for selecting one of the first measuring mode and the second measuring mode;

wherein in the first measuring mode, the first measuring section measures the red blood cell sample, the second measuring section measures the first white blood cell sample, and the third measuring section measures the hemoglobin sample; and wherein in the second measuring mode, the first measuring section measures the red blood cell sample, the second measuring section measures the second white blood cell sample, and the third measuring section measures the hemoglobin sample.

DETAILED DESCRIPTION OF THE PREFERRED EMBODIMENTS

The preferred embodiments of the present invention are described hereinafter with reference to the drawings.

[General Structure]

Figure 1:
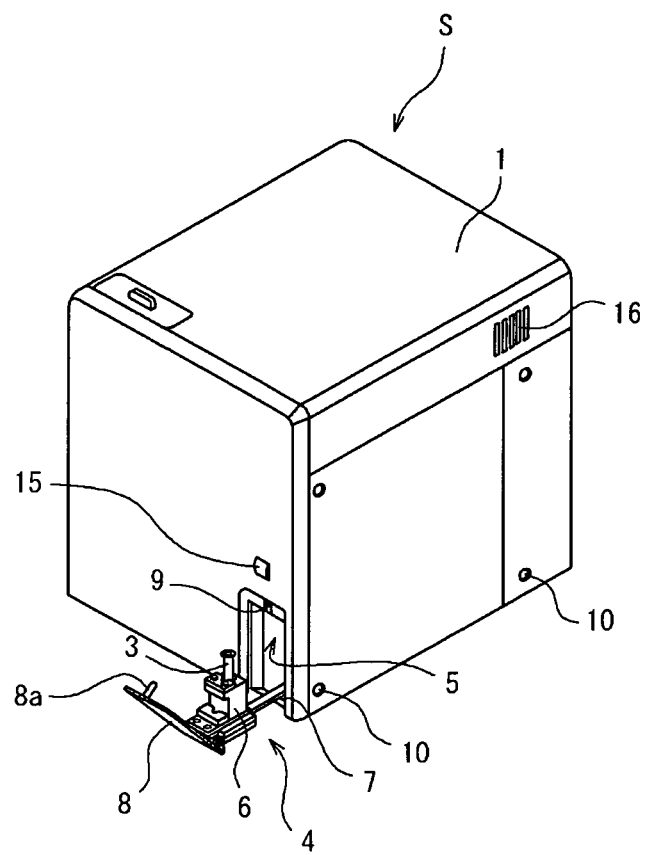
FIG. 1 is a perspective view of the entire sample analyzer of a first embodiment of the present invention.
Figure 2:
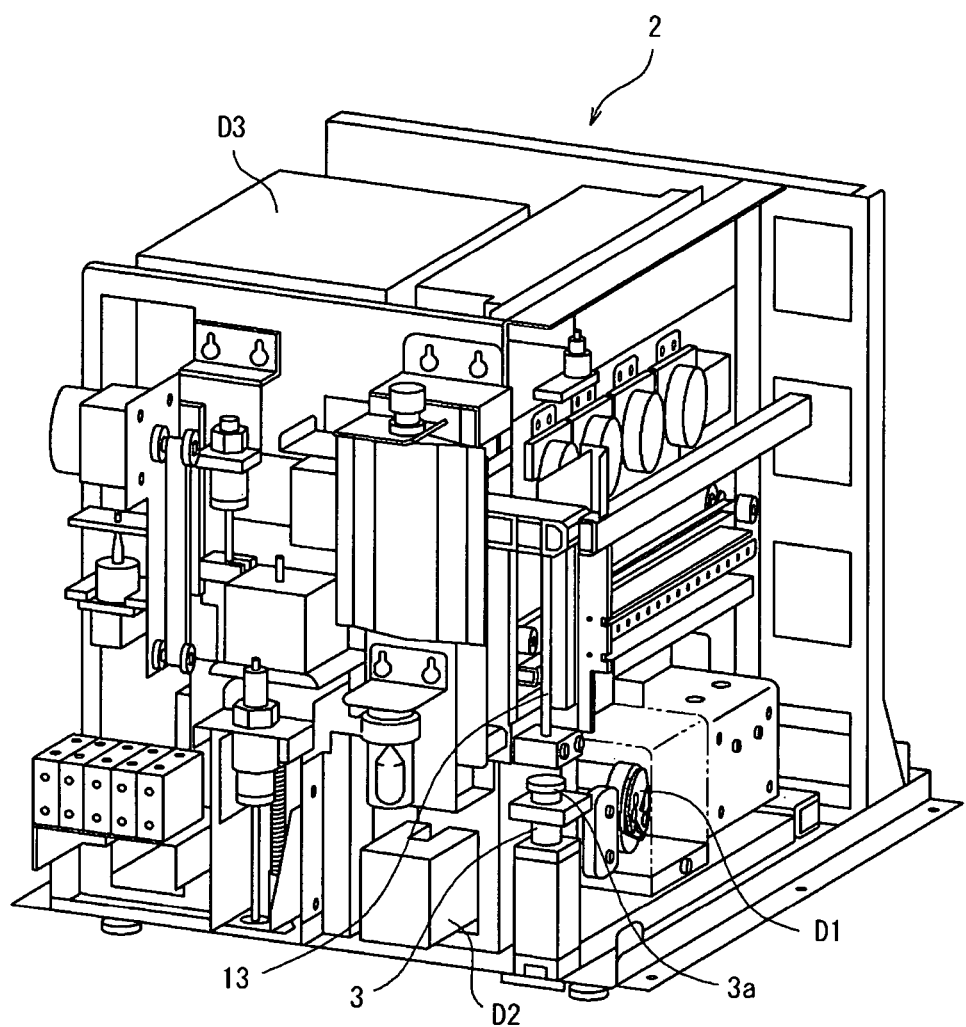
FIG. 2 is a perspective view showing the sample analyzer of FIG. 1 with the casing removed.
Figure 3:
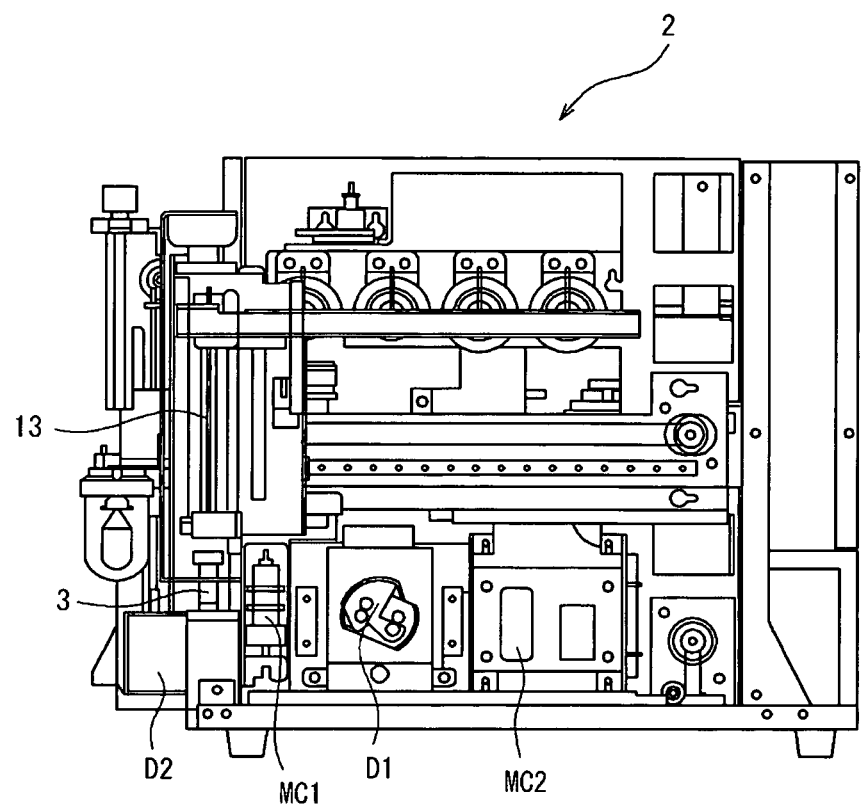
FIG. 3 is a front view showing the sample analyzer of FIG. 1 with the casing removed.

FIG. 1 is a perspective view of the entire sample analyzer S of an embodiment of the present invention; FIG. 2 is a perspective view of the sample analyzer S with the casing 1 removed; and FIG. 3 is a front view with the casing removed.

Figure 4:
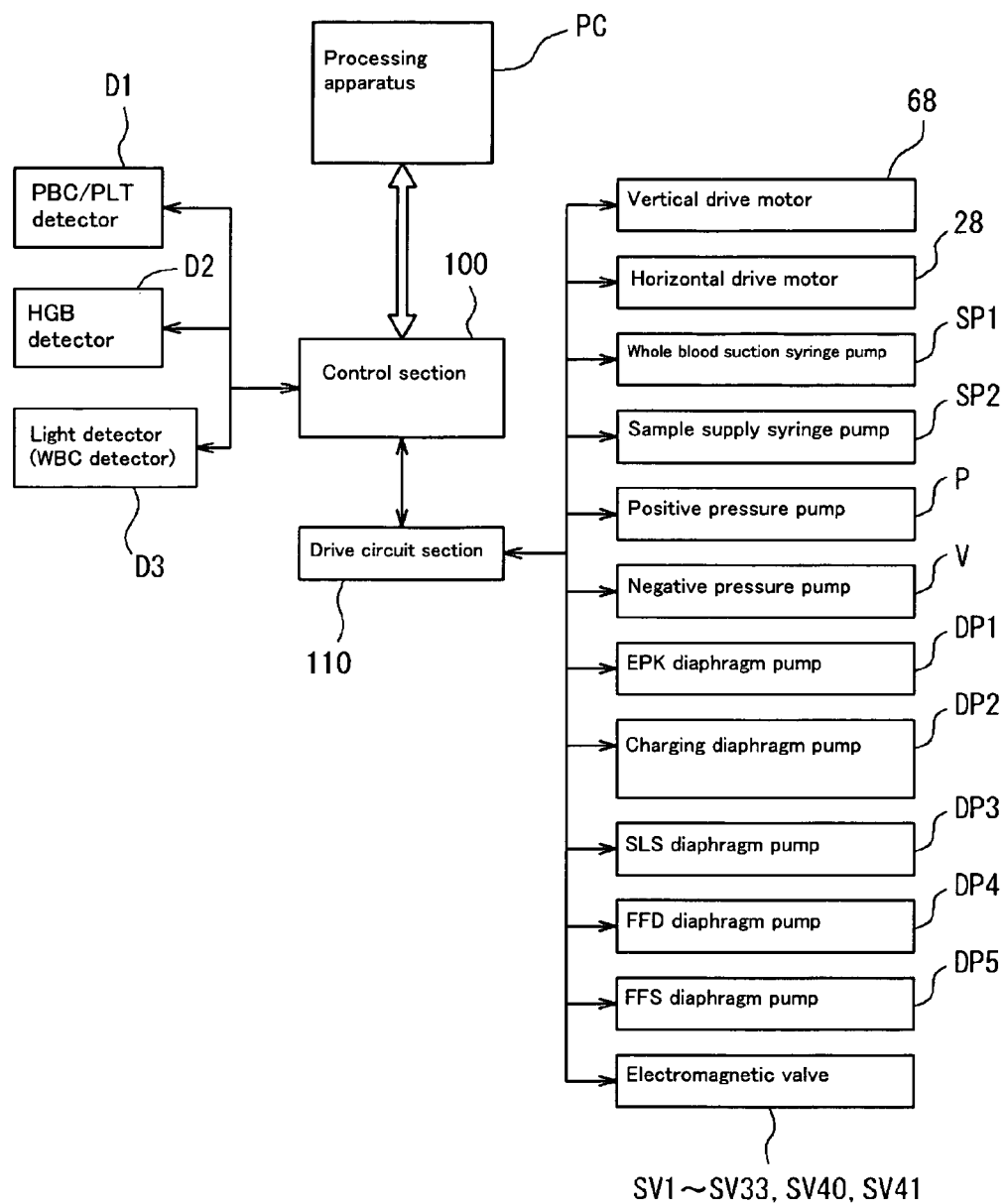
FIG. 4 is a control block diagram of the sample analyzer.

The sample analyzer S is connected to a processing apparatus PC (typically, a personal computer on which is installed the necessary computer programs) having a display, input device, CPU, memory and the like so as to be capable of communication, and the sample analyzing system of the present embodiment is configured by the sample analyzer S and the processing apparatus PC (refer to FIG. 4).

The processing apparatus PC has sample analyzer software installed to operate the sample analyzer S, perform various settings related to analysis, display analysis results and the like, and is capable of issuing instructions to the sample analyzer S, and receiving measurement data from the sample analyzer S through communication with the sample analyzer The sample analyzer S is an apparatus (blood analyzer) for analyzing (measuring and analyzing) blood (sample) contained within a sealed container type blood collection tube 3 (initial container in which the sample was collected), and is mainly configured by an apparatus body 2, and casing 1 in which the apparatus 2 is housed.

The casing 1 is made of synthetic resin, steel treated to be corrosion resistant or the like, and is fixed to the apparatus body 2 using fixing means such as bolts or the like. An opening part 5 is formed in the bottom right side part of one surface (left side surface in FIG. 1) of the casing 1, and collection tubes 3 can be inserted into the interior of the apparatus body 2 through the opening part 5. That is, a slider 7, which has an installation surface 6 for installing the collection tubes 3 near the end part, is arranged so as to emerge and retract from the opening part 5 at the bottom of one end of the apparatus body 1. A cover 8 for closing the opening part 5 is provided at the leading end of the slider 7 so as to be freely rotatable, and a force exerted by a spring not shown in the drawing forces the cover 8 so as to be inclined to the exterior side at a predetermined angle. When the apparatus is in a non-operating state (this state can be displayed on the exterior by having a lamp within the button 15 provided on one surface of the casing 1 turned OFF) and the button 15 is pressed, the slider 7 advances outward from the apparatus body 2. Thus, although the opening part 5 is closed by the cover 8 when the apparatus is in the non-operating state, the engagement of the a projection 8a of the cover 8 with a concavity 9 formed on the perimeter of the opening part 5 is released by the advance of the slider 7 outward from the apparatus body 2, such that the cover 8 is opened. Furthermore, the cover 8 is inclined to the exterior side at a predetermined angle by the force exerted by the spring when the engagement of the projection 8a and the concavity 9 is released.

A concavity (not shown in the drawing) capable of accepting the insertion of the bottom of a collection tube 3 is formed in the top surface of the installation surface 6; when the bottom of a collection tube 3 is inserted in this concavity and the button 15 is pressed, the slider 7 retracts within the apparatus body 2 and the collection tube 3 is set at a predetermined position. Then, the cover 8 is raised against the force exerted by the spring, and the opening part 5 is closed by the cover 8. At this time, the cover 8 is prevented from opening by the engagement of the projection 8a with the concavity 9. The apparatus is set so as to allow a sample suction process and similar subsequent processes when a detection means, such as a microswitch or the like, detects that the opening part 5 has been reliably closed by the cover 8.

A part (right side surface in FIG. 1) of the side surface of the casing 1 is bolted to the apparatus body 2 so allow ease of maintenance and inspection inside the apparatus body 2. In FIG. 1, an exhaust port is provided mainly to expel heat generated within the apparatus body 2 by a fan (not shown in the drawing) to outside of the apparatus body 2.

The apparatus body 2 is provided with a sample set section 4 for placing the collection tubes 3 at a predetermined position within the apparatus, sample preparation section for preparing an analysis sample by measuring and diluting blood within the collection tube 3, and measuring sections D1, D2, D3 for performing measurements of the diluted blood.

[Sample Set Section]

The sample set section 4 is the site in which the collection tube 3, which contains the sample (blood) in a sealed state, is placed at a predetermined position, and is configured by the installation surface 6, the slider 7 and a drive source (not shown in the drawing), such as a stepping motor or the like for driving the slider 7.

[Sample Preparation Section]

The sample preparation section is a site for preparing samples for use in various types of analysis by suctioning a predetermined quantity of blood from within the collection tube 3, and mixing with a reagent in a first mixing chamber (first container; HGB/RBC chamber) MC1 or second mixing chamber (second container) MC2; and is provided with a suction tube 13 for puncturing a stopper 3a, which seals the collection tube 3, and suctioning the sample from within the collection tube 3, a horizontal drive unit for horizontally driving the suction tube 13, and a vertical drive unit for vertically driving the suction tube 13. A stepping motor 28 is provided as the horizontal drive unit, and a stepping motor 68 is provided as the vertical drive unit (refer to FIG. 4).

The suction tube 13 has a channel that extends in the length direction in the interior, and is not specifically limited in the present invention insofar as the suction opening for suctioning sample or air is formed in the vicinity of the tip.

[Sample Container]

Figure 5:
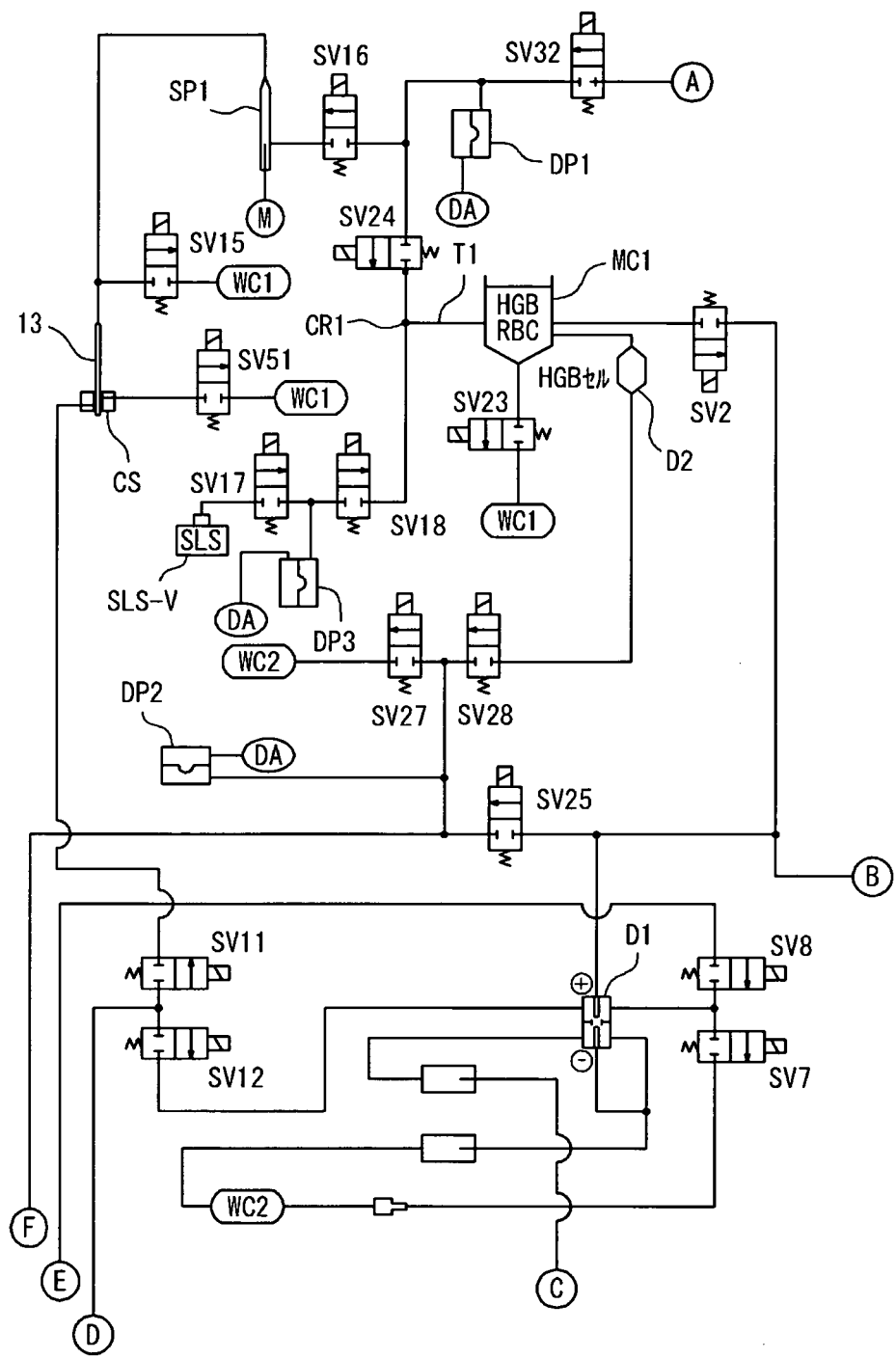
FIG. 5 shows the front half of the flow circuit diagram of the sample analyzer of FIG. 1.
Figure 6:
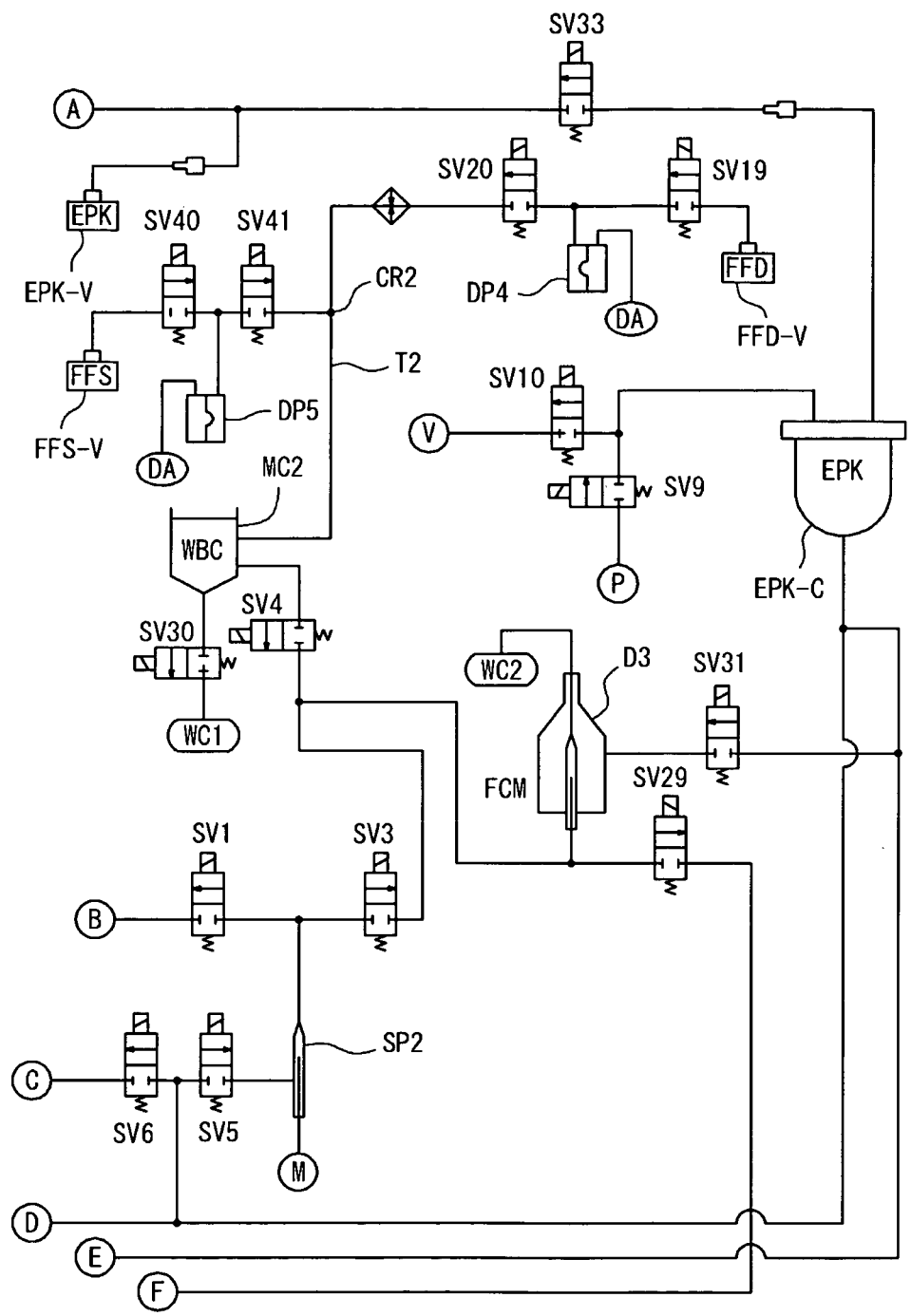
FIG. 6 shows the back half of the flow circuit diagram of the sample analyzer of FIG. 1.
Figure 7:
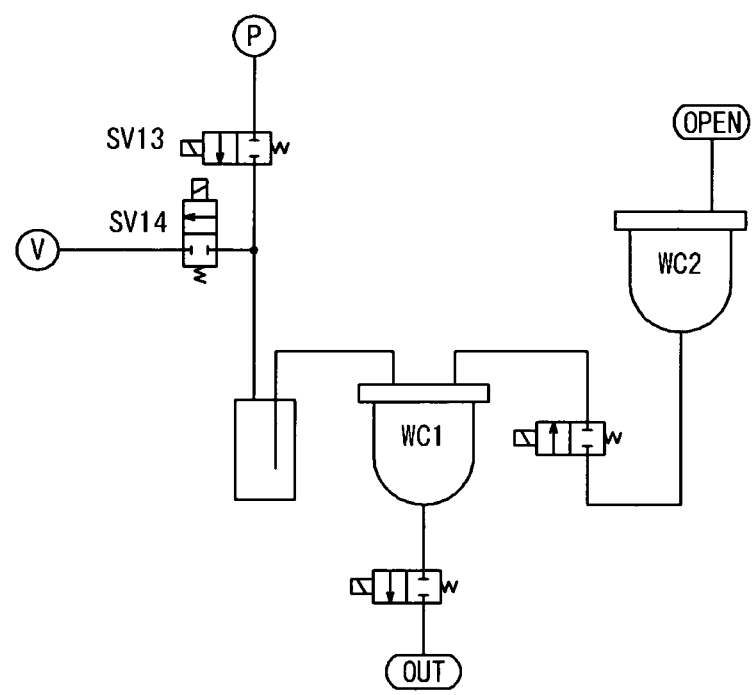
FIG. 7 is a flow circuit diagram of the surroundings of the drainage chamber.
Figure 8:
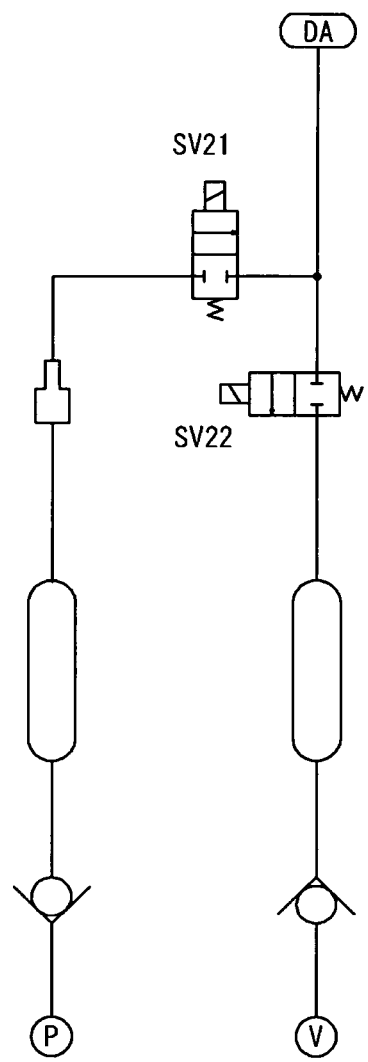
FIG. 8 is a flow circuit diagram of the surroundings of the diaphragm pump.
Figure 9:
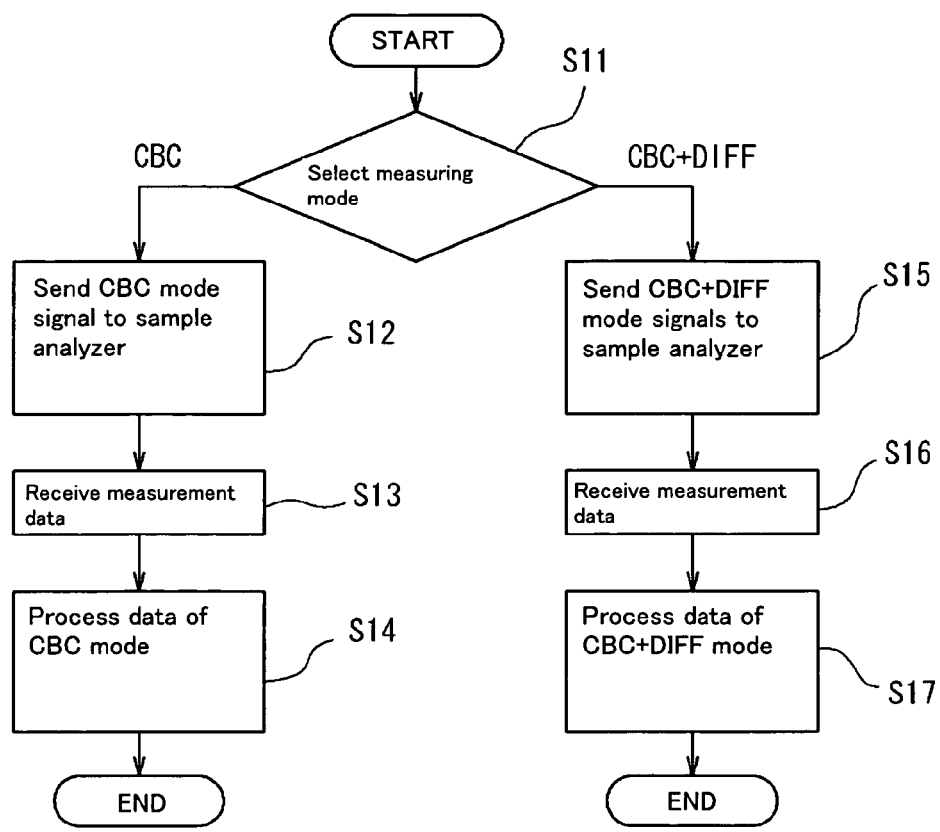
FIG. 9 is a flow chart related to measuring mode selection.

As shown in the channel diagram of FIGS. 5 and 6, reagent containers containing reagent can be provided in the apparatus body 2, and the reagent containers can be connected to the channel. Specifically, the reagent containers used in the present embodiment are diluting liquid container EPK-V for containing diluting liquid (washing liquid) EPK, hemoglobin hemolyzing reagent container SLS-V for containing hemoglobin hemolyzing reagent, white blood cell classification hemolyzing reagent container (common reagent container) FFD-V for containing white blood cell classification hemolyzing reagent FFD for hemolyzing red blood cells, and white blood cell classification staining liquid container (special reagent container) FFS-V for containing white blood cell classification staining liquid FFS. In the present embodiment, for example, a stomatolizer 4DL (Sysmex Corporation) is used as the common reagent, that is, the white blood cell classification hemolyzing reagent FFD, and, for example, stomatolizer 4DS (Sysmex corporation) is used as the special reagent, that is, white blood cell classification staining liquid FFS.

[Reagent Providing Section]

The suction tube 13 and a whole blood suction syringe pump SP1 are provided as a sample providing section for providing sample from the collection tube 3 to the first mixing chamber MC1 and/or second mixing chamber MC2. The suction tube 13 suctions a fixed quantity of whole blood sample from the collection tube 3 by the whole blood suction syringe pump SP1, then moves to the position of the first mixing chamber MC1 and second mixing chamber MC2, and dispenses some of the fixed quantity of whole blood to the respective chambers MC1 and MC2 by the whole blood suction syringe pump SP1.

[Reagent Providing Section]

The diluting liquid container EPK-V and the hemolyzing agent container SLS-V are connected to the first mixing chamber MC1 so as to be capable of providing reagent. That is, diluting liquid can be supplied from the diluting liquid container EPK-V to the first mixing chamber MC1 by the dilution liquid providing (for EPK) diaphragm pump DP1; the EPK diaphragm pump DP1 configures the diluting liquid reagent providing section.

Furthermore, hemolyzing reagent can be supplied from the hemolyzing reagent container SLS-V to the first mixing chamber MC1 by the hemolyzing reagent providing (for SLS) diaphragm pump DP3; the SLS diaphragm pump DP3 configures the hemolyzing reagent providing section.

The hemolyzing reagent container FFD-V and staining liquid container FFS-V are connected to the second mixing chamber MC2, which is the holding container of the present invention, so as to be capable of providing reagent. That is, hemolyzing reagent can be supplied from the hemolyzing reagent container FFD-V to the second mixing chamber MC2 by the hemolyzing reagent providing (for FFD) diaphragm pump DP4; the FFD diaphragm pump DP4 configures the hemolyzing reagent providing section (common reagent providing section).

Furthermore, staining liquid can be supplied from the staining liquid container FFS-V to the second mixing chamber MC2 by the staining liquid providing (for FFS) diaphragm pump DP5; the FFS diaphragm pump DP5 configures the staining liquid reagent providing section (special reagent providing section).

is

[Reagent Providing Channel]

The reagent providing channel from the diluting liquid container EPK-V to the first mixing chamber MC1, and the reagent providing channel from the hemolyzing reagent container SLS-V to the first mixing chamber MC1 become confluent at the confluence point CR1 in their course, and the reagent providing channel T1 that is common to both reagents is connected to the first mixing chamber MC1 (refer to FIG. 5). Accordingly, although the first mixing chamber MC1 is provided by two kinds of reagent, the structure can be simplified because the first mixing chamber MC1 has only one reagent supply aperture.

The reagent providing channel from the hemolyzing reagent container FFD-V to the second mixing chamber MC2, and the reagent providing channel from the staining liquid container FFS-V to the second mixing chamber MC2 become confluent at the confluence point CR2 in their course, and the reagent providing channel T2 that is common to both reagents is connected to the second mixing chamber MC2 (refer to FIG. 6). Accordingly, although the second mixing chamber MCs is provided by two kinds of reagent, the structure can be simplified because the second mixing chamber MC2 has only one reagent supply aperture.

The reagent providing channels T1 and T2 may also be provided for each reagent. That is, two reagent supply apertures are provided for each chamber MC1 and MC2.

[Measuring Section]

The previously mentioned measuring sections D1, D2, D3 include a first measuring section D1 provided for measurements relating to red blood cells and platelets, a second measuring section D2 provided for measurements relating to hemoglobin, and a third measuring section D3 provided for measurements relating to white blood cells.

The first mixing chamber MC1 is the site for preparing samples for analyses relating to red blood cells, platelets, and hemoglobin; a sample prepared in the first mixing chamber MC1 is used for measurements by the first measuring section D1 and second measuring section D2.

The second mixing chamber MC2 is the site for preparing samples for analyses relating to white blood cells; a sample prepared in the second mixing chamber MC2 is used for measurements by the third measuring section D3.

[First Measuring section; RBC/PLT Detecting Section]

The first measuring section D1 is configured as an RBC/PLT detecting section for performing RBC measurement (red blood cell count) and PLT measurement (platelet count). The RBC/PLT detecting section D1 can measure the RBC and PLT using a sheath flow DC detection method.

[Second Measuring Section; HGB Measuring Section]

The second measuring section D2 is configured as an HGB detecting section for performing HGB measurement (measuring the amount of blood pigment in the blood). The HGB detecting section D2 can perform HGB measurement using a SLS-hemoglobin method.

[Third Measuring Section; Light Detecting Section]

The third measuring section D3 is configured as a light detecting section capable of performing WBC measurement (white blood cell count) and DIFF measurement (white blood cell classification). The light measuring section D3 is capable of performing WBC measurement and DIFF measurement using a flow cytometric method with a semiconductor laser. The structure of the third measuring section D3 is described in detail later.

[Control Section]

As shown in FIG. 4, the apparatus body 2 is provided with a control section 100 for controlling the sample preparation sections and measuring sections D1, D2, and D3. The apparatus body 2 is also provided with electromagnetic valves SV1~SV33, SV40, and SV41 disposed within the channels configuring the sample preparation sections, and drive circuit 110 for driving the various types of pump motors 28, 68, SP1, SP2, P, V, DP1, DP2, DP3, DP4, and DP5; the control section 100 drives the electromagnetic valves and the like through a drive circuit section 110.

The control section 100 is capable of communicating with the processing apparatus PC through a communication interface not shown in the drawing, so as to send and receive various signals and data to and from the processing apparatus PC.

[Types of Measuring Modes]

The sample analyzer S has two measuring modes relating to the measurements performed by the third measuring section D3 white blood cells in the blood of the sample. A first measuring mode is the CBC measuring mode for measuring basic items such as the numbers of white blood cells (WBC), red blood cells (RBC), and platelets (PLT), hemoglobin concentration, and hematocrit value and the like. A second measuring mode is the CBC+DIFF measuring mode for measuring the above basic items, and classifying white blood cells into five classifications of neutrophils, lymphocytes, monocytes, eosinophils, basophils.

[Mode Selection]

A user of the sample analyzing system can select whether to perform measurements in the CBC measuring mode (first measuring mode) or CBC+DIFF measuring mode (second measuring mode) using the processing apparatus PC. The processing apparatus PC has a screen display function that allows a user to select either the CBC or CBC+DIFF on the screen, and a function for receiving input for selecting either the CBC or CBC+DIFF from a mouse or keyboard or the like as selection functions, and configures a mode selecting section having these functions.

Specifically, when a user selects CBC in the selection mode (step S11), the processing apparatus PC transmits instructions to execute the CBC mode measurements to the sample analyzer S (step S12). Then, the sample analyzer S operates so as to perform measurements in the CBC measuring mode, and the measurement data are transmitted to the processing apparatus PC. When the processing apparatus PC receives the CBC measurement data from the sample analyzer S (step S13), the CBC measurement data are subjected to data processing (step S14), and the processed results are either saved to a file or displayed on the screen in a predetermined display format.

When a user selects CBC+DIFF in the measuring mode selection (step S11), the processing apparatus PC transmits instructions to execute CBC+DIFF mode measurements to the sample analyzer S (step S15). The sample analyzer S receives the CBC+DIFF mode instruction signals, and operates so as to perform measurements in the CBC+DIFF measuring mode, and transmits the measurement data to the processing apparatus PC. When the processing apparatus PC receives the CBC+DIFF measurement data from the sample analyzer S (step S16), the CBC+DIFF measurement data are subjected to data processing (step S17), and the processed results are either saved to a file or displayed on the screen in a predetermined display format.

[CBC Measuring Mode; First Measuring Mode]

The sample analyzer S prepares a CBC measuring mode sample (first mode sample) by mixing a whole blood sample (11 μL) and hemolyzing reagent (1 mL), and measures the CBC measuring mode sample by flow cytometry using the light detector D3 in the third measuring section to obtain the white blood cell count.

Figure 10:
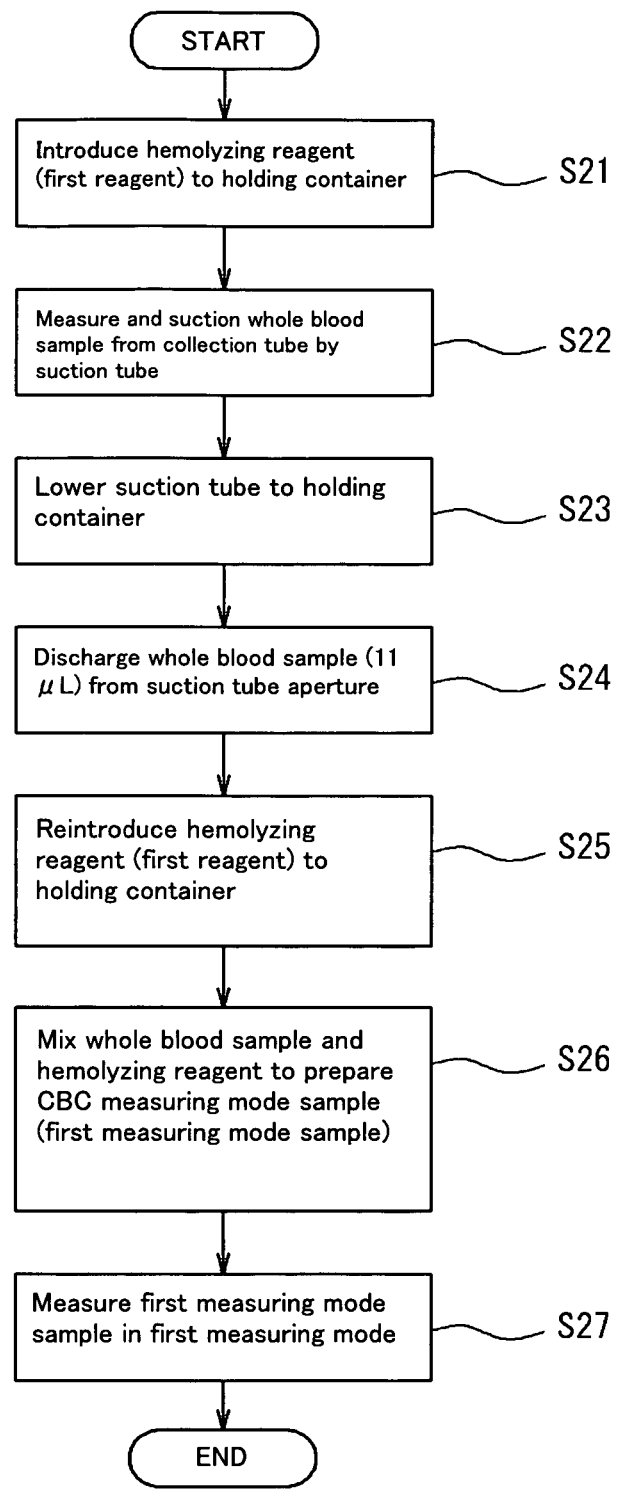
FIG. 10 is a flow chart of a first measuring mode.

FIG. 10 shows the operation sequence of the sample analyzer S in the CBC measuring mode. The operation sequence is described below with reference to the flow channel diagrams of FIGS. 5 through 8. First, the common reagent of hemolyzing reagent FFD (0.5 mL) is supplied from the common reagent container of hemolyzing reagent container FFD-V to the holding container that is the second mixing chamber MC2 (step S21). A hemolyzing reagent for white blood cell classification is used as the common reagent, and the hemolyzing reagent is used in common in the second measuring mode, that is, the CBC+DIFF measuring mode. A diluting liquid may also be included as a common reagent. Alternatively, a diluting liquid may also be used individually as a common reagent depending on the measurement content.

In step S21, specifically, by opening the valve SV19 and closing the valve SV20, and opening the valve SV22 and closing the valve S21, the FFD diaphragm pump D4 produces a negative pressure to supply 0.5 mL of the hemolyzing reagent FFD from the hemolyzing reagent container FFD-V to the FFD diaphragm pump D4.

Then, by closing the valve SV19 and opening the valve SV20, and opening the valve S21 and closing the valve S22, the FFD diaphragm pump D4 produces a positive pressure to supply the 0.5 mL of hemolyzing reagent FFD to the second mixing chamber MC2.

Finally, by opening the valve S19 and closing the valve S20, and closing the valve S21 and opening the valve S22, the FFD diaphragm pump D4 produces a negative pressure and 0.5 mL of the hemolyzing reagent FFD is again supplied from the hemolyzing reagent container FFD-V to the FFD diaphragm pump D4.

Then, the whole blood sample is measured and suctioned from the collection tube 3 by the suction tube (piercer) 13 (step S22). Step S22, specifically entails the insertion of the suction tube 13 into the collection tube 3, and suctioning a measured quantity (20 μL) of whole blood sample by actuating the whole blood suction syringe pump SP1.

Then, the suction tube 13 is removed from the collection tube 3, and the suction tube 13 is lowered to the second mixing chamber MC2 (step S23). In this state, the 11 μL whole blood sample (the part of the sample suctioned in step S22) is discharged from the suction aperture of the suction tube 13 into the second mixing chamber MC2 by the actuation of the whole blood suction syringe pump SP1 (step S24).

After discharge is completed, hemolyzing reagent FDD is again introduced into the second mixing chamber MC2 by the FDD diaphragm pump D4 (step S25), and the influx mixes the whole blood sample to prepare the CBC measuring mode sample (first measuring mode sample) in which the red blood cells have undergone lysis in the second mixing chamber MC2 (step S26).

Then, the CBC measuring mode sample (first measuring mode sample) is subjected to measurements in the CBC measuring mode (first measuring mode) by the WBC detection section (light detector; third measuring section) D3 (step S27). In step S27, specifically, by opening the valves SV4, SV29, and SV22 and closing the valve SV21, the charging diaphragm pump DP2 is actuated and accurately charged with 1.0 mL of CBC measuring mode sample. Then, the valves SV4, SV29, and S22 are closed, and the charging to the WBC detection section D3 is completed.

Thereafter, by opening the valves SV9 and SV31, the sheath fluid (diluting liquid) EPK is supplied from the EPK holding container EPK-C to the WBC detection section D3. Next, the valve SV3 is opened with the valve SV1 in the closed state, and the sample providing syringe pump SP2 is actuated and the measurement is performed in the WBC detection section D3.

The charging diaphragm pump DP2 and the sample providing syringe pump SP2 configure the supplying section for supplying the CBC measuring mode sample (first measuring mode sample) and/or the CBC+DIFF measuring mode sample (second measuring mode sample) to the WBC detection section D3.

[CBC+DIFF Measuring Mode; Second Measuring Mode]

In the CBC+DIFF measuring mode, the sample analyzer S prepares the CBC+DIFF measuring mode sample (second measuring mode sample) by mixing whole blood sample (11 µL), white blood cell hemolyzing reagent (1 mL), and white blood cell staining liquid (20 µL), and measures the CBC+DIFF measuring mode sample by flow cytometry with the light detector D3. The white blood cell count is measured and the white blood cells are measured in five classifications in this measurement in which the measurement of the white blood cell count overlaps the first measuring mode.

Figure 11:
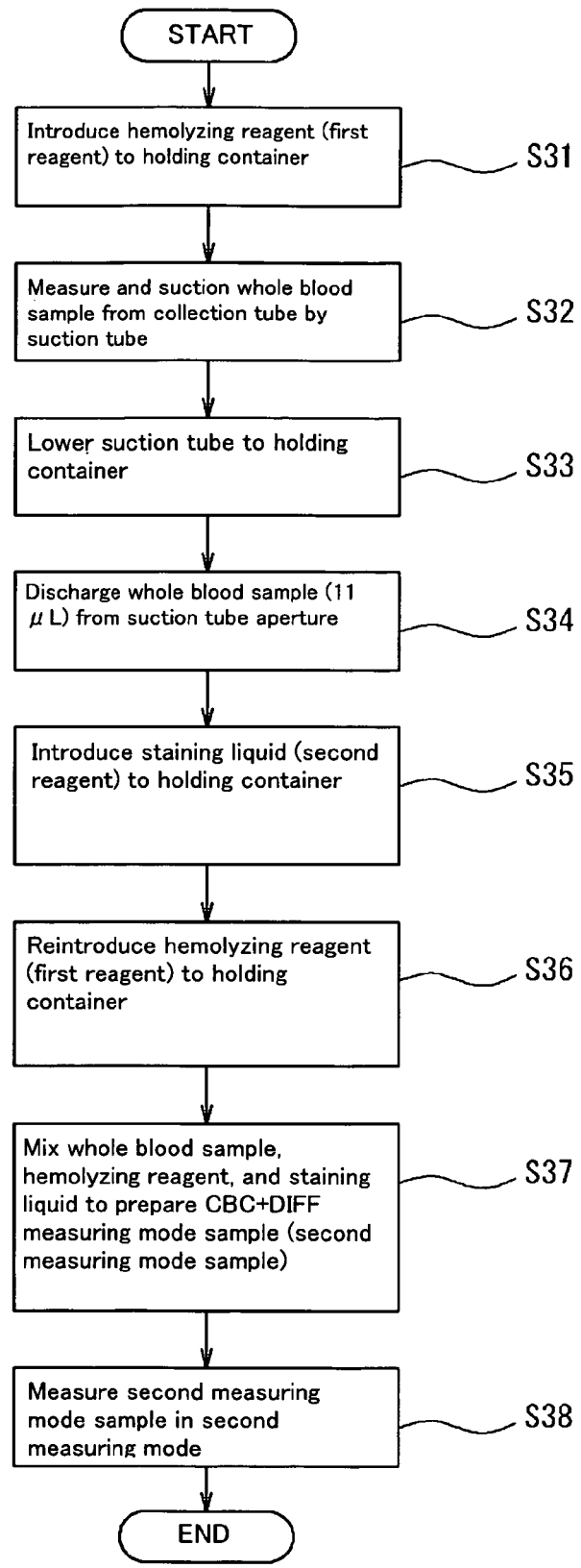
FIG. 11 is a flow chart of a second measuring mode.

FIG. 11 shows the operation sequence of the sample analyzer S in the CBC+DIFF measuring mode. First, the common reagent of hemolyzing FFD (0.5 mL) is supplied from the hemolyzing reagent container FFD-V to the second mixing chamber MC2 (step S31).

In step S31, specifically, the valve SV19 is opened and valve SV20 is closed, and valve SV22 is opened and valve S21 is closed, and the FFD diaphragm pump D4 produces a negative pressure to supply 0.5 mL of the hemolyzing reagent FFD from the hemolyzing reagent container FFD-V to the FFD diaphragm pump D4.

Then, by closing the valve SV19 and opening the valve SV20, and opening the valve S21 and closing the valve S22, the FFD diaphragm pump D4 produces a positive pressure to supply the 0.5 mL of hemolyzing reagent FFD to the second mixing chamber MC2.

Finally, by opening the valve S19 and closing the valve S20, and closing the valve S21 and opening the valve S22, the FFD diaphragm pump D4 produces a negative pressure and 0.5 mL of the hemolyzing reagent FFD is again supplied from the hemolyzing reagent container FFD-V to the FFD diaphragm pump D4.

Then, the whole blood sample is measured and suctioned from the collection tube 3 by the suction tube (piercer) 13 (step S32). Step S32, specifically entails the insertion of the suction tube 13 into the collection tube 3, and suctioning a measured quantity (20 µL) of whole blood sample by actuating the whole blood suction syringe pump SP1.

Then, the suction tube 13 is removed from the collection tube 3, and the suction tube 13 is lowered to the second mixing chamber MC2 (step S33). In this state, the 11 µL whole blood sample (the part of the sample suctioned in step S32) is discharged from the suction aperture of the suction tube 13 into the second mixing chamber MC2 by the actuation of the whole blood suction syringe pump SP1 (step S34).

After discharge is completed, the staining liquid (special reagent) FFS is introduced into the second mixing chamber MC2 (step S35). Step S35, specifically, by opening the valve SV22 and closing the valve SV21 when the staining liquid supply valve SV41 is closed actuates a negative pressure in the staining liquid supply diaphragm pump (FFS diaphragm pump) DP5 to supply the 20 µL staining liquid FFS to the FFS diaphragm pump DP5.

Finally, by opening the valve SV 40 and the closing the valve SV41, and closing the valve SV22 and actuating a positive pressure in the FFS diaphragm pump DP5, the 20 µL staining liquid FFS is introduced into the second mixing chamber MC2. Other reagents, such as, for example, diluting liquid and buffering liquid may be included in the special reagent, and diluting liquid and buffering liquid may also be used individually as a special reagent.

Next, the hemolyzing reagent (common reagent) FFD is introduced into the second mixing chamber MC2 (step S36). That is, 0.5 mL of the hemolyzing reagent FFD is introduced into the second mixing chamber MC2 using the FFD diaphragm pump DP4 and closing the valves SV22 and SV19 and opening the valves SV21 and SV20, and the influx mixes with the whole blood sample to prepare the CBC+DIFF measuring mode sample (second measuring mode sample) in which the red blood cells have undergone lysis in the second mixing chamber MC2 (step S26).

After the staining reagent that was unused in the CBC measuring mode has been supplied to the second mixing chamber MC2, the hemolyzing reagent that is the common reagent in both modes is supplied to the second mixing chamber MC2 to wash the common reagent providing channel T with the hemolyzing reagent. Accordingly, even when the CBC measuring mode is executed after the CBC+DIFF measuring mode, unnecessary staining liquid is prevented from contaminating the CBC measuring mode sample.

Then, the CBC+DIFF measuring mode sample (second measuring mode sample) is subjected to the measurements of the CBC+DIFF measuring mode (second measuring mode) by the WBC detecting section (light detector) D3. In step S38, specifically, by opening the valves SV4, SV29, and SV22 and closing the valve SV21, the charging diaphragm pump DP2 is actuated and accurately charged with 1.0 mL of CBC+DIFF measuring mode sample. Then, the valves SV4, SV29, and S22 are closed, and the charging to the WBC detection section D3 is completed.

Thereafter, by opening the valves SV9 and SV31, the sheath fluid (diluting liquid) EPK is supplied from the EPK holding container EPK-C to the WBC detection section. Next, the valve SV3 is opened with the valve SV1 in the closed state, and the sample providing syringe pump SP2 is actuated and the measurement is performed in the WBC detection section D3.

[Light Detector (WBC Detection Section)]

Figure 12:
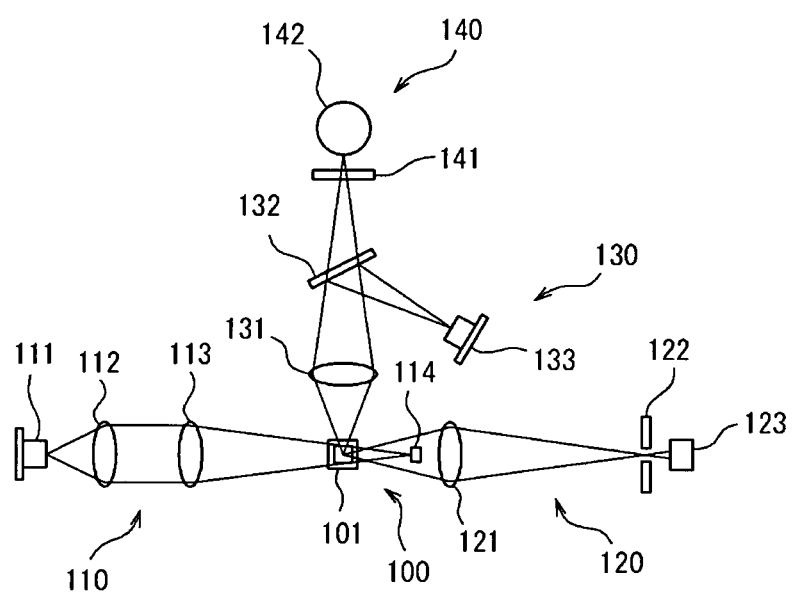
FIG. 12 is a brief structural diagram of the light detector.

FIG. 12 shows the essential structure of the third measuring section, light detector (WBC detection section) D3. The light detector D3 has a sheath flow system 100, beam spot forming system 110, forward scattered light receiving system 120, side scattered light receiving system 130, and side fluorescent light receiving system 140, and measures the light when the sample (first mode sample or second mode sample) is fed into a flow cell 101 creating a flow, and the blood cells included in the flow within the flow cell 101 are irradiated with semiconductor laser light.

The sheath flow system 100 produces a flow in which the blood cells are in a single line encapsulated in sheath fluid within the flow cell 100, and thus improves the reproducibility and accuracy of the blood cell count.

The beam spot system 110 is configured so as to irradiate the flow cell 101 by having the light emitted from a semiconductor laser 111 pass through a collimator lens 112 and condenser lens 113. The beam spot system 110 is also provided with a beam stopper 114.

The forward scattered light receiving system 120 is configured so as to collect the forward scattered light by means of a collective lens 121, and receive the light passing through a pinhole 122 by a photodiode (forward scattered light receiving section) 123.

The side scattered light receiving section 130 is configured so as to collect the forward scattered light by a side collective lens 131, and reflect part of the light to a dichroic mirror 132, which is then received by a photodiode (side scattered light receiving section) 133.

A phenomenon occurs in which the direction of the scattered light is changed by particles such as blood cells. Information relating to the size and material of these particles can be obtained by detecting the scattered light. In particular, information relating to the size of the particle (blood cell) can be obtained from the forward scattered light. Furthermore, information relating to the interior part of the particle can be obtained from the side scattered light. When laser light irradiates a blood cell particle, the intensity of the side scattered light is dependent on the complexity (nuclear shape, size, density, and granularity) of the interior part of the cell. Accordingly, white blood cell classification measurements and other measurement can be performed using the characteristics of the side scattered light intensity.

The side scattered light receiving section 140 is configured so that the light passing through the dichroic mirror 132 passes through a spectral filter 141, and is received by a photomultiplier (fluorescent light receiving section) 142.

When light irradiates fluorescent matter, such as a stained blood cell, light is produced that has a longer wavelength than the wavelength of the irradiating light. The intensity of the fluorescent light is stronger when the matter is highly stained, and information can be obtained relating to the degree of staining of the blood cell by measuring the fluorescent light intensity. Therefore, white blood cell classification measurement and other measurements can be performed according to the differences in the (side) fluorescent light intensities.

When light is received by each light receiving section 123, 133, 142, each light receiving section 123, 133, 142 outputs an electric pulse signal. Measurement data are created by the electric pulse signals. The measurement data are transmitted from the sample analyzer SA to the processing apparatus PC (steps S13 and S16), and the measurement data are subjected to processing and analysis in the processing apparatus PC.

In the CBC measuring mode, the processing apparatus PC calculates the number of white blood cells included in the CBC measuring mode sample by performing white blood cell particle size analysis base don the scattered light received by the scattered light receiving sections. More specifically, the white blood cell count is calculated based on the light received by the forward scattered light receiving section 123.

Figure 14:
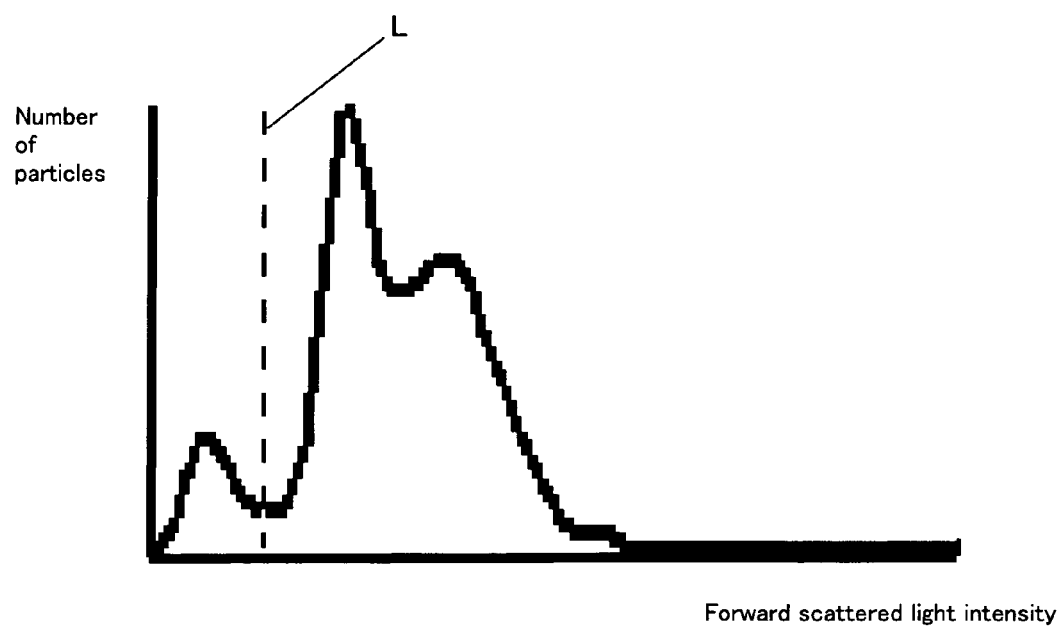
FIG. 14 is a histogram showing the white blood cell frequency distribution.

FIG. 14 shows a histogram of white blood cells displayed on a processing apparatus PC. The histogram shows the forward scattered light intensity plotted on the X-axis, and the particle number plotted on the Y-axis. The line L shown in this histogram separates the white blood cells from ghosts that include hemolyzed red blood cells, and the line L is set by the processing apparatus PC automatically detecting troughs in the histogram. In this histogram, the side of the line L on which the forward scattered light intensity is small depicts ghosts, and the side of the line L on which the forward scatter light intensity is large depicts white blood cells. therefore, the number of white blood cells can be calculated by determining the total number of particles on the side of the line L on which the forward scatter light intensity is large.

Figure 13:
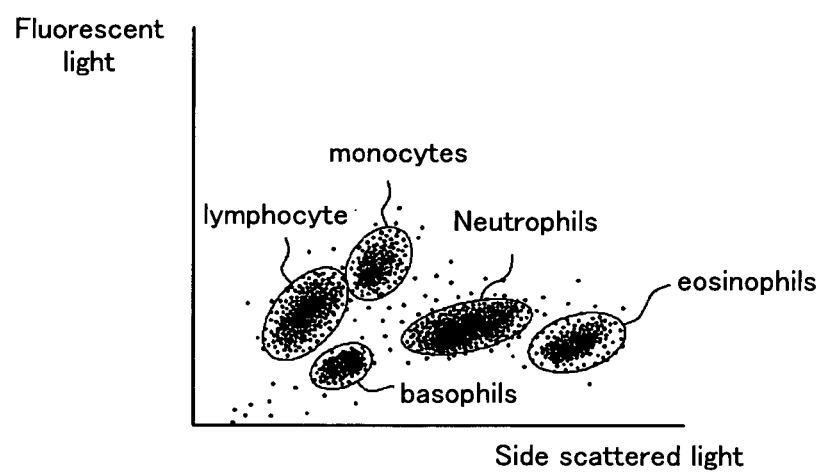
FIG. 13 is a scattergram showing five types of white blood cells.

Furthermore, in the CBC+DIFF measuring mode, the processing apparatus PC calculates the number of white blood cells included in the CBC+DIF measuring mode sample, and classifies the white blood cells (five classifications: neutrophils, lymphocytes, monocytes, eosinophils, basophils) based on the fluorescent light (side fluorescent light) received by the fluorescent light receiving section and the scattered light received by the scattered light receiving sections. FIG. 13 shows a scattergram of the white blood cell classifications displays on the processing apparatus PC. The scattergram plots the side scattered light intensity on the X axis and the fluorescent light intensity on the Y axis, and has five separate totals for neutrophils, lymphocytes, monocytes, eosinophils, basophils. As can be understood from this scattergram, white blood cells are detected in five separate cell groups by the processing apparatus PC. The processing apparatus PC performs various processes such as calculating the number of blood cells include number of each classification, and the percentage of numbers between classifications.

The white blood cell count determined in the CBC+DIFF measuring mode may also be the total number of hemocytes included in five hemocyte groups of the scattergram, and may also be calculated from the histogram of FIG. 14.

The remaining whole blood sample that was not used in the white blood cell analyses, among the whole blood samples suctioned by the suction tube 13, are used red blood cell and hemoglobin measuring samples in the first mixing chamber MC1, and these samples are measured in the first measuring section D1 and second measuring section D2.

When there is a reagent component common to the first measuring mode and second measuring mode (hemolyzing reagent in the present embodiment), and the reagent (hemolyzing reagent) of the first measuring mode and the reagent (hemolyzing reagent and staining liquid mixture) of the second measuring mode are prepared separately beforehand, then it may occur that the common reagent (hemolyzing reagent) of one mode may be wasted when the other measuring mode is used more frequently; however, the common reagent (hemolyzing reagent) used as the common component in the first measuring mode and the special reagent (staining liquid) required in the second measuring mode can be mixed to prepare the second measuring mode sample, as in the embodiment described above. Therefore, waste of the common component reagent (hemolyzer) is reduced.

[RBC/PLT Measurement and HGB Measurement]

The RBC/PLT measurement and HGB measurement executed in both the CBC mode and CBC+DIFF measuring mode are described below. These measurements are executed in parallel with the previously mentioned CBC measurement or CBC+DIFF measurement.

When the RBC/PLT measurement and HGB measurement are performed, both an RBC/PLT measurement mixed sample, and an HGB measurement mixed sample are required. Since the reagent for preparing the RBC/PLT measurement mixed sample, and the reagent for preparing the HGB measurement mixed sample are different, separate preparation processes are required, and normally two mixing chambers are required to prepare these mixed samples.

Figure 15:
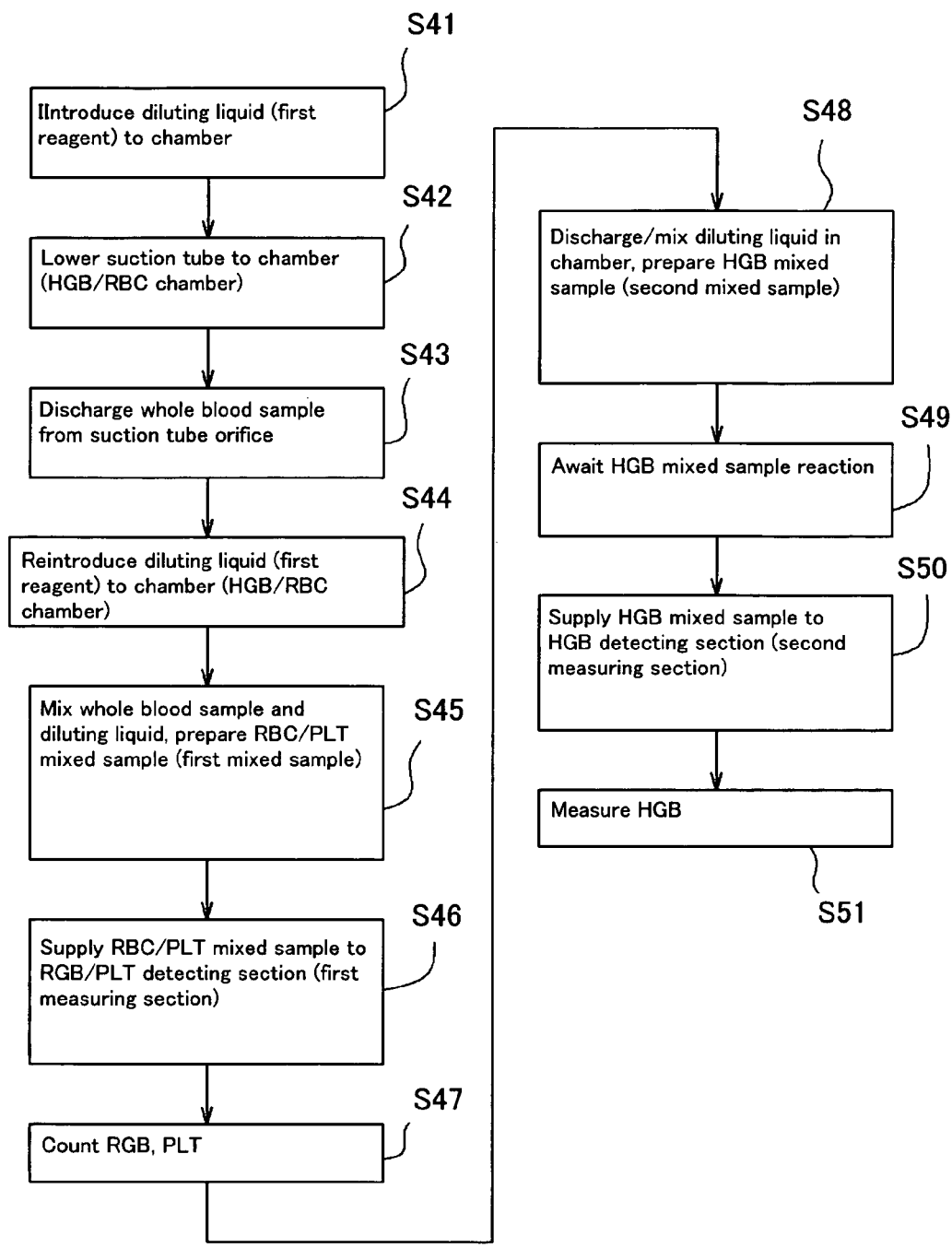
FIG. 15 is a flow chart showing the measurement sequence of the RBC/PLT measurement and HGB measurement.
Figure 16:
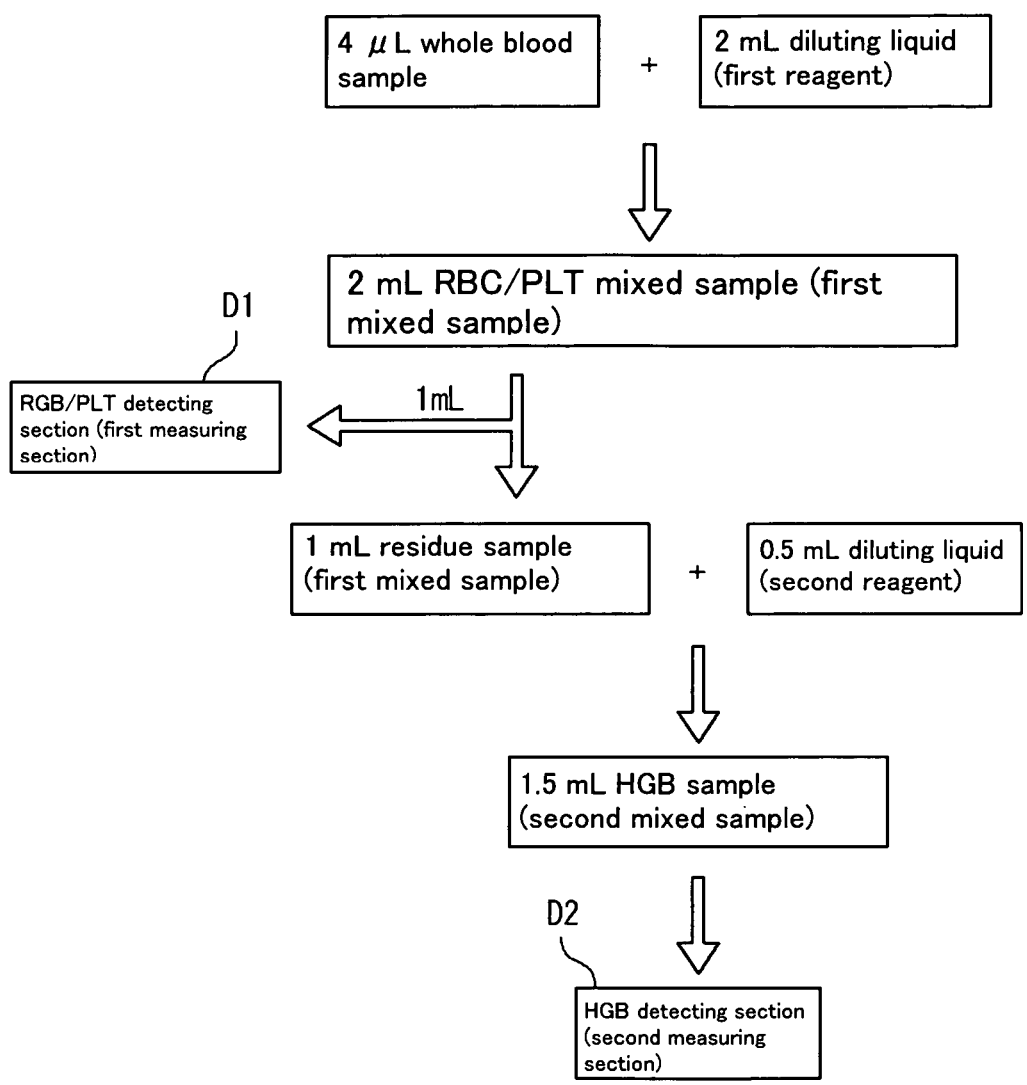
FIG. 16 is a brief view of the mixed sample preparation process.

In contrast, in the present embodiment, two mixed samples can be prepared in a single mixing chamber (first mixing chamber; HGB/RBC chamber) MC1. The measurement sequence that includes the preparation sequence is described in detail below based on FIGS. 15 and 16.

[RBC/PLT Measurement Mixed Sample Preparation and Measurement]

First, in step S22 or S32 (refer to FIGS. 10 and 11), whole blood is measured and suctioned (20 μL) from the blood collection tube 3 by the suction tube (piercer) 13. Specifically, the whole blood sample is measured and suction by inserting the suction tube 13 into the collection tube 3, and suctioning a measured quantity (20 µL) of whole blood sample by actuating the whole blood suction syringe pump SP1.

Thereafter, the first reagent of diluting liquid EPK is supplied to the first mixing chamber MC1 (step S41). Specifically, in step S41, the valve SV23 is opened approximately 1.0 seconds to discharge fluid inside the first mixing chamber MC1. Then, the valve SV21 and valve SV24 are opened, and 1.0 mL of diluting liquid EPK is supplied to the first mixing chamber MC1 using the diluting liquid (EPK) diaphragm pump D1 to which diluting liquid EPK has been resupplied beforehand. Thereafter, the valves SV21 and SV24 are closed, the valves SV22 and SV32 are opened, and diluting liquid EPK is resupplied to the EPK diaphragm pump DP1.

Next, the suction tube 13 is lowered to the first mixing chamber MC1 (step S42), and 4 µL of whole blood sample is discharged from the suction orifice of the suction tube 13 to the first mixing chamber MC1 (step S43). Steps S42 and S43 are executed immediately after the execution of steps S24 or S34 (refer to FIGS. 10 and 11).

After the discharge is completed, the first reagent of diluting liquid EPK is resupplied to the first mixing chamber MC1 (step S44). Specifically, in step S44, after the discharge is completed, the valves SV22 and SV32 are closed and the valves SV21 and SV24 are opened to resupply 1.0 mL of, diluting liquid EPK to the first mixing chamber using the EPK diaphragm pump DP1. Thus, the whole blood sample (4 µL) and diluting liquid EPK (2 mL) are mixed in the first mixing chamber MC1, and the first mixed sample (RBC/PLT measurement sample) is prepared (step S45).

After the first mixed sample has been prepared, the valves SV21 and SV24 are closed, and the valves SV22 and Sv32 are opened to resupply the diluting liquid EPK to the EPK diaphragm pump.

Then, part of the first mixed sample (RBC/PLT measurement mixed sample) is supplied to the RBC/PLT detecting section D1 (step S46). Specifically, in step S46, 1.0 mL (part of the first mixed sample in the first mixing chamber MC1) of the first mixed sample is charged to the flow path between the first mixing chamber MC1 and RBC/PLT detecting section D1 by opening the valves SV2 and SV25 and using the charging diaphragm pump DP2. Then, the valves SV2, SV25, SV22, and SV32 are closed, and the charging is completed. finally, the valves SV8 and SV9 are opened, and the sheath fluid is supplied to the RBC/PLT detecting section D1.

The charged first mixed sample is supplied to the RBC/PLT detecting section D1, and the RBC/PLT measurement is performed (step S47). Specifically, in step S47, the valve SV1 is opened and the sample supplying syringe pump SP2 is actuated to supply the first mixed sample charged in the channel to the RBC/PLT detecting section DP1, and the number of RBC and PLT are counted. then, the valves SV8, SV9, and SV1 are closed, and counting is ends.

The charging diaphragm pump DP2 and the sample supplying syringe pump SP2 configure a first sample supplying section for supplying a first mixed sample of the RGB/PLT measurement mixed sample from the first mixing chamber MC1 to the RBC/PLT detecting section D1.

[HGB Measurement Mixed Sample Preparation and Measurement]

Even after the RBC/PLT measurement has ended, there is still a residue of the first mixed sample in the first mixing chamber MC1. A hemolytic agent SLS is supplied to the first mixing chamber MC1 containing the residual sample to prepare the second mixed sample of HGB measurement mixed sample. Specifically in step S48, the hemolytic agent SLS is supplied to the first mixing chamber MC1 by opening the valves SV21 and SV18, and using the hemoglobin hemolytic agent (SLS) diaphragm pump DP3 which has been resupplied with hemolytic agent SLS beforehand. Thus, the hemolytic agent SLS and first mixed sample are mixed, and the HGB measurement mixed sample (second mixed sample) including a mixture of the first mixed sample (1.0 mL) and hemolytic agent SLS (0.5 mL) is prepared.

Then, the reaction of the HGB measurement mixed sample is awaited (step S49). During the optional time during which the reaction is awaited, the valves SV21 and SV27 are opened, and the charging diaphragm pump DP2 is discharged in preparation for the next charging.

Subsequently, the valves SV22 and SV28 are opened, the HGB measurement mixed sample is starts charging to the HGB detecting section D2, and the valves SV22 and SV28 are closed to end the charging (step S50). Then, the HGB measurement is performed (step S51).

The charging diaphragm pump DP2 configures the second mixed sample supplying section for supplying the second mixed sample of HGB measurement mixed sample from the first mixing chamber MC1 to the HGB detecting section D2.

The present invention is not limited to the above described embodiment. For example, the first measuring mode and the second measuring mode are not limited to the modes described in the above embodiment, inasmuch as a mode for measuring the number of red blood cells (RBC) may be used as the first measuring mode, and a mode for measuring the number of red blood cells (RBC) and the measuring reticulocytes may be used as the second measuring mode. In this case, a swelling agent for expanding the red blood cells may be used as the common reagent, and a staining liquid for inducing a staining reaction of the reticulocytes may be used as the special reagent of the second measuring mode. That is, measurement is performed using a first mode sample of a mixture of the swelling agent and blood specimen in the first measuring mode, and measurement is performed using a second mode sample of a mixture of staining liquid and blood specimen in the second measuring mode.

Although the first mode sample and the second mode sample are mixed in a common holding container (second mixing chamber MC2) in the above embodiment, the sample of each mode may also be mixed in separate holding containers.

Although the measurements are performed in the first measuring mode and measurements are performed in the second measuring mode by the common measuring section D3, these measurements may also be performed by separate measuring sections.

Although the sample analyzing system is configured by a sample analyzer S and a separate processing apparatus PC in the above embodiment, the functions of both the sample analyzer S and the processing apparatus PC may be installed in a single apparatus.

Moreover, in the case of the above embodiment, the measuring modes of the sample analyzing system or sample analyzer are not limited to two modes and may be three or more modes. In this case, the reagent used may include a common reagent used commonly in a first measuring mode, second measuring mode, and third measuring mode, and a first special reagent may be used in the second measuring mode, and a second special reagent may be used in the third measuring mode.

The first mode sample used in the first measuring mode may be prepared by mixing a sample and the common reagent, the second mode sample used in the second measuring mode may be prepared by mixing a sample and common reagent and first special reagent, and a third mode sample used in the third measuring mode may be prepared by mixing a sample and common reagent and a second special reagent.

Alternatively, the third mode sample used in the third measuring mode may also be prepared by mixing a sample and common reagent and first special reagent and second special reagent. In this case, the first special reagent becomes a common reagent between the second mode sample and the third mode sample.

Although the first mode sample contains hemolytic agent, and the second mode sample contains hemolytic agent and staining liquid in the above embodiments, the sample analyzer may also be configured to have the first mode sample contain hemolytic agent, and the second mode sample contain a special reagent other than a hemolytic agent.

Furthermore, although the RBC/PLT measurement mixed sample and the HGB measurement mixed sample are prepared in the first mixing chamber MC1, and the CBC measurement mixed sample (first mode sample) and CBC+DIFF measurement mixed sample (second mode sample) are prepared in the second mixing chamber MC2 in the above embodiments, the present invention is not limited to this arrangement inasmuch as, for example, three mixing chambers may be provided such that the RBC/PLT measurement mixed sample is prepared in a first chamber, the residue RBC/PLT measurement mixed sample remaining after the mixed sample has been supplied to the measuring section may be supplied to the second mixing chamber and a hemoglobin hemolytic agent SLS may be supplied to the second chamber to prepare the HGB measurement mixed sample in the second chamber, and the CBC measurement mixed sample and CBC+DIFF measurement mixed sample may be prepared in the third chamber. Moreover, the CBC measurement mixed sample and the CBC+DIFF measurement mixed sample may be prepared in different chambers.

What is claimed is:

1. A blood analyzer capable of operating in a first measuring mode for measuring a sample and a second measuring mode for measuring a sample, comprising:
   a sample provider for providing a blood sample;
   a common reagent provider for providing a hemolyzing reagent as a common reagent used in the first measuring mode and the second measuring mode;
   a special reagent provider for providing a staining liquid as a special reagent used in the second measuring mode;
   a chamber;
   a measuring section for measuring the blood sample;
   a display;
   an input device; and
   a controller programmed to execute operations of:
   controlling the display to display a screen which allows the selection of either the first measuring mode or the second measuring mode by using the input device;
   when the first measuring mode is selected, controlling the sample provider and the common reagent provider so as to provide the blood sample and the hemolyzing reagent to the chamber to prepare a first mode sample in the chamber, and controlling the measuring section to measure the first mode sample for acquiring a number of white blood cells; and
   when the second measuring mode is selected, controlling the sample provider, the common reagent provider, and the special reagent provider so as to provide the blood sample, the hemolyzing reagent and the staining liquid to the chamber to prepare a second mode sample in the chamber, and controlling the measuring section to measure the second mode sample for acquiring a number of white blood cells and classifying white blood cells into a plurality of subclasses of white blood cells.

2. The blood analyzer of claim 1 wherein measuring items in the first measuring mode and measuring items in the second measuring mode are overlapped partially.

3. The blood analyzer of claim 1 wherein the hemolyzing reagent and the staining liquid are provided into the chamber from a reagent providing channel which is connected with the chamber.

4. The blood analyzer of claim 1 wherein the measuring section comprises
   a light source for irradiating light to flow of one of the first mode sample and the second mode sample, and
   a light detector for receiving the light irradiated on the flow.

5. The blood analyzer of claim 4 wherein the light detector comprises
   a scattered light detector for detecting scattered light generated by irradiating the light from the light source to the flow, and
   a fluorescent light detector for detecting fluorescent light generated by irradiating the light from the light source to the flow.

6. The blood analyzer of claim 5 wherein, in the first measuring mode, the controller processes scattered light information detected by the scattered light detector, and
   in the second measuring mode, the controller processes scattered light information detected by the scattered light detector and fluorescent light information detected by the fluorescent light detector.

7. A blood analyzer capable of operating in a first measuring mode for measuring a sample and a second measuring mode for measuring a sample, comprising:
   a common chamber commonly used to prepare a first mixture used in the first measuring mode and a second mixture used in the second measuring mode;
   a sample provider for providing a blood sample into the common chamber;
   a common reagent provider for providing, into the common chamber, a hemolyzing reagent as a common reagent used in the first measuring mode and the second measuring mode; and
   a special reagent provider for providing, into the common chamber, a staining liquid as a special reagent used in the second measuring mode;
   a controller programmed to:
   in the first measuring mode, control the sample provider and the common reagent provider so as to provide the blood sample and the hemolyzing reagent into the common chamber to prepare the first mixture in the common chamber; and
   in the second measuring mode, control the sample provider, the common reagent provider and the special reagent provider so as to provide the blood sample, the hemolyzing reagent and the staining liquid into the common chamber to prepare the second mixture in the common chamber; and
   a measuring section for measuring the first mixture for acquiring a number of white blood cells, and measuring the second mixture for acquiring a number of white blood cells and classifying white blood cells into a plurality of subclasses of white blood cells.

8. A blood analyzer for analyzing a blood sample, comprising:
a chamber;
a sample provider for providing the blood sample to the chamber;
a first reagent provider for providing a diluting liquid to the chamber;
a second reagent provider for providing a hemolyzing reagent to the chamber;
a first measuring section for measuring red blood cells contained in a first mixed sample prepared from the blood sample and the diluting liquid;
a first mixed sample provider for providing the first mixed sample from the chamber to the first measuring section;
a second measuring section for measuring hemoglobin contained in a second mixed sample prepared from the blood sample, the diluting liquid and the hemolyzing reagent;
a second mixed sample provider for providing the second mixed sample from the chamber to the second measuring section; and
a controller programmed to:
control the sample provider and the first reagent provider so as to provide the blood sample and the diluting liquid to the chamber to prepare the first mixed sample in the chamber, and control the first mixed sample provider so as to provide a part of the first mixed sample from the chamber to the first measuring section; and
control the second reagent provider so as to provide the hemolyzing reagent to the chamber to prepare the second mixed sample from the hemolyzing reagent and the first mixed sample remaining in the chamber.

9. The blood analyzer of claim 8,
wherein the first measurement section further measures platelets.

10. The blood analyzer of claim 8,
wherein the first reagent provider provides the diluting liquid to the chamber before and after the blood sample is provided to the chamber by the sample provider.

11. The blood analyzer of claim 8, further comprising:
a second chamber;
a third reagent provider for providing a second hemolyzing reagent to the second chamber;
a fourth reagent provider for providing a staining liquid to the second chamber; and
a third measuring section for measuring white blood cells contained in a third mixed sample prepared from the blood sample, the second hemolyzing reagent, and the staining liquid,
wherein the sample provider provides the blood sample to the chamber and the second chamber.

12. A blood analyzer for analyzing a blood sample, comprising:
a blood sample provider for providing a first blood sample and a second blood sample, the first and second blood samples being split from a blood sample;
a first reagent provider for providing a diluting liquid;
a second reagent provider for providing a first hemolyzing reagent;
a third reagent provider for providing a second hemolyzing reagent;
a first chamber for preparing a first mixed sample for measurement of red blood cells and/or platelets and a second mixed sample for measurement of hemoglobin;
a second chamber for preparing a third mixed sample for measurement of white blood cells;
a first measuring section for measuring the red blood cells and/or the platelets contained in the first mixed sample;
a second measuring section for measuring the hemoglobin contained in the second mixed sample;
a third measuring section for measuring the white blood cells contained in the third mixed sample; and
a controller programmed to:
control the blood sample provider and the first reagent provider so as to provide the first blood sample and the diluting liquid to the first chamber to prepare the first mixed sample in the first chamber, and control the first measuring section so as to measure the red blood cells and/or the platelets contained in a part of the first mixed sample;
control the second reagent provider so as to provide the first hemolyzing reagent to the first chamber to prepare, in the first chamber, the second mixed sample from the first hemolyzing reagent and a different part of the first mixed sample which remains in the first chamber without being used for the measurement by the first measuring section; and
control the blood sample provider and the third reagent provider so as to provide the second blood sample and the second hemolyzing reagent to the second chamber to prepare the third mixed sample in the second chamber.

13. The blood analyzer of claim 7,
wherein, in the second measuring mode, the controller controls the common reagent provider and the special reagent provider such that the hemolyzing reagent is provided into the common chamber in which the staining liquid has already been provided.

14. The blood analyzer of claim 13,
wherein, in the second measuring mode, the controller controls the sample provider, the common reagent provider, and the special reagent provider such that the hemolyzing reagents are provided into the common chamber before and after provision of the staining liquid in the common chamber.

15. The blood analyzer of claim 14,
wherein, in the second measuring mode, the controller controls the sample provider, the common reagent provider, and the special reagent provider such that the blood sample is provided into the common chamber between the first provision of the hemolyzing reagent and the second provision of the hemolyzing reagent.

16. The blood analyzer of claim 15,
wherein, in the second measuring mode, the controller controls the sample provider, the common reagent provider, and the special reagent provider such that the blood sample is provided into the common chamber between the first provision of the hemolyzing reagent and provision of the staining liquid.

17. The blood analyzer of claim 12, further comprising
a mixed sample transporter for transporting the first mixed sample from the first chamber to the first measuring section, wherein
the controller controls the mixed sample transporter so as to transport the part of the first mixed sample from the first chamber to the first measuring section, and controls the second reagent provider so as to provide the first hemolyzing reagent to the first chamber after the part of the first mixed sample has been transported out of the first chamber.

18. The blood analyzer of claim 12, wherein
the blood sample provider comprises a suction tube which suctions the blood sample from a sample container and dispenses the first blood sample and the second blood sample into the first chamber and the second chamber, respectively.

19. The blood analyzer of claim 12, further comprising a fourth reagent provider for providing a staining liquid, wherein when acquiring a number of white blood cells, the controller controls the third reagent provider so as to provide the second hemolyzing reagent to the second chamber to prepare the third mixed sample from the second blood sample and the second hemolyzing reagent in the second chamber, when classifying white blood cells into a plurality of subclasses of white blood cells, the controller controls the third reagent provider and the fourth reagent provider so as to provide the second hemolyzing reagent and the staining liquid to the second chamber to prepare a fourth mixed sample from the second blood sample, the second hemolyzing reagent and the staining liquid in the second chamber, and the third measuring section is configured to measure white blood cells contained in the fourth mixed sample.

20. The blood analyzer of claim 12, wherein the controller controls the blood sample provider and the first reagent provider such that the first blood sample is provided to the first chamber after the diluting liquid has been provided to the first chamber.

* * * * *